United States Patent
Kuwabara

(10) Patent No.: US 10,345,459 B2
(45) Date of Patent: Jul. 9, 2019

(54) RADIOGRAPHY APPARATUS AND RADIOGRAPHY METHOD

(71) Applicant: FUJIFILM CORPORATION, Minato-ku, Tokyo (JP)

(72) Inventor: Takeshi Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/118,459

(22) Filed: Aug. 31, 2018

(65) Prior Publication Data

US 2019/0011576 A1    Jan. 10, 2019

Related U.S. Application Data

(63) Continuation of application No. PCT/JP2016/086221, filed on Dec. 6, 2016.

(30) Foreign Application Priority Data

Mar. 28, 2016   (JP) ................... 2016-063951

(51) Int. Cl.
   *G01T 1/208*   (2006.01)
   *G01T 1/17*    (2006.01)
   (Continued)

(52) U.S. Cl.
   CPC ............ *G01T 1/208* (2013.01); *A61B 6/4233* (2013.01); *A61B 6/4241* (2013.01);
   (Continued)

(58) Field of Classification Search
   CPC ..... G01T 1/208; G01T 1/2023; G01T 1/2018; G01T 1/17; A61B 6/54; A61B 6/4233;
   (Continued)

(56) References Cited

U.S. PATENT DOCUMENTS

| 10,120,082 | B2 * | 11/2018 | Ergler | ............ | A61B 6/4241 |
| 2012/0018653 | A1 * | 1/2012 | Bowers | ............ | G02B 1/005 |
| | | | | | 250/505.1 |

(Continued)

FOREIGN PATENT DOCUMENTS

| JP | H02-41082 A | 2/1990 |
| JP | 2012-107887 A | 6/2012 |

(Continued)

OTHER PUBLICATIONS

International Search Report issued in International Application No. PCT/JP2016/086221 dated Feb. 14, 2017.

(Continued)

*Primary Examiner* — David P Porta
*Assistant Examiner* — Gisselle Gutierrez
(74) *Attorney, Agent, or Firm* — Solaris Intellectual Property Group, PLLC

(57) ABSTRACT

A radiography apparatus includes: a first radiation detector that includes plural pixels accumulating charge corresponding to emitted radiation; a second radiation detector that is stacked on a side of the first radiation detector opposite to a side on which the radiation is incident and includes plural pixels accumulating charge corresponding to the emitted radiation; a first control unit that performs control for reading the charge accumulated in the pixels of the first radiation detector while the charge is accumulated in the pixels of the first radiation detector and the second radiation detector; and a second control unit that starts control for reading the charge accumulated in the pixels of the second radiation detector while the charge is accumulated in the pixels of the first radiation detector and the second radiation detector at a time different from a time when the first control unit starts the control.

12 Claims, 10 Drawing Sheets

(51) Int. Cl.
　　　*H04N 5/32*　　　(2006.01)
　　　*H04N 5/341*　　(2011.01)
　　　*A61B 6/00*　　　(2006.01)
　　　*G01T 1/20*　　　(2006.01)
　　　*G01T 1/202*　　(2006.01)
　　　*H04N 5/357*　　(2011.01)
　　　*H04N 5/359*　　(2011.01)
　　　*H01L 27/148*　　(2006.01)
　　　*H01L 27/146*　　(2006.01)

(52) U.S. Cl.
　　　CPC ............ *A61B 6/4266* (2013.01); *A61B 6/482* (2013.01); *A61B 6/505* (2013.01); *A61B 6/54* (2013.01); *G01T 1/17* (2013.01); *G01T 1/2018* (2013.01); *G01T 1/2023* (2013.01); *H01L 27/14856* (2013.01); *H04N 5/32* (2013.01); *H04N 5/341* (2013.01); *H04N 5/359* (2013.01); *H04N 5/3577* (2013.01); *A61B 6/5258* (2013.01); *A61B 6/548* (2013.01); *H01L 27/14663* (2013.01)

(58) Field of Classification Search
　　　CPC ....... A61B 6/4266; A61B 6/00; A61B 6/5258; H04N 5/359; H04N 5/3577; H04N 5/341; H04N 5/32

USPC .......................................................... 250/362
See application file for complete search history.

(56)　　　　　　References Cited

U.S. PATENT DOCUMENTS

2012/0197080 A1　　8/2012　Murayama
2014/0037045 A1*　2/2014　Dafni .................... A61B 6/032
　　　　　　　　　　　　　　　　　　　　　　378/5

FOREIGN PATENT DOCUMENTS

| JP | 2012-157559 A | 8/2012 |
| JP | 2013-11553 A | 1/2013 |
| JP | 2014-195481 A | 10/2014 |

OTHER PUBLICATIONS

Written Opinion of the ISA issued in International Application No. PCT/JP2016/086221 dated Feb. 14, 2017.

* cited by examiner

RADIOGRAPHY APPARATUS AND RADIOGRAPHY METHOD

CROSS-REFERENCE TO RELATED APPLICATIONS

This application is a continuation application of International Application No. PCT/JP2016/086221, filed on Dec. 6, 2016, which is incorporated herein by reference in its entirety. Further, this application claims priority from Japanese Patent Application No. 2016-063951, filed on Mar. 28, 2016, the disclosure of which is incorporated by reference herein in its entirety.

BACKGROUND

Technical Field

The present disclosure relates to a radiography apparatus and a radiography method.

Related Art

In the related art, a radiography apparatus has been known which includes two radiation detectors that include a plurality of pixels accumulating charge corresponding to emitted radiation and are provided so as to be stacked. In addition, a technique has been known which captures a motion picture using one radiation detector and captures a still image using the other radiation detector in this type of radiography apparatus (see JP2014-195481A).

However, in a case in which the two radiation detectors are used to capture radiographic images, an operation of reading charge accumulated in the one radiation detector causes electrical noise in the other radiation detector.

In the technique disclosed in JP2014-195481A, while a motion picture is being captured by the one radiation detector, the other radiation detector is turned off to reduce the influence of the noise. In addition, in the technique disclosed in JP2014-195481A, while a still image is being captured by the other radiation detector, the one radiation detector is turned off to reduce the influence of the noise.

However, in the technique disclosed in JP2014-195481A, since one radiation detector is turned off, one of two radiation detectors is turned on and only the radiation detector that is being driven captures a radiographic image. That is, in the technique disclosed in JP2014-195481A, a radiographic image is captured in a state in which charge is accumulated in only one of two radiation detectors.

SUMMARY

The present disclosure provides a radiography apparatus and a radiography method that can reduce the influence of noise in a case in which charge accumulated in pixels of each of two radiation detectors is read.

According to a first aspect of the invention, there is provided a radiography apparatus comprising: a first radiation detector that includes a plurality of pixels accumulating charge corresponding to emitted radiation; a second radiation detector that is provided so as to be stacked on a side of the first radiation detector opposite to a side on which the radiation is incident and includes a plurality of pixels accumulating charge corresponding to the emitted radiation; a first control unit that performs control for reading the charge accumulated in the pixels of the first radiation detector in a state in which the charge is accumulated in the pixels of each of the first radiation detector and the second radiation detector; and a second control unit that starts control for reading the charge accumulated in the pixels of the second radiation detector in a state in which the charge is accumulated in the pixels of each of the first radiation detector and the second radiation detector at a time different from a time when the first control unit starts the control.

According to a second aspect of the invention, in the radiography apparatus according to the first aspect, the first control unit may perform control for reading the charge accumulated in the pixels of the first radiation detector in a state in which the charge is held in the pixels of the second radiation detector and the second control unit may perform control for reading the charge accumulated in the pixels of the second radiation detector in a state in which the charge is held in the pixels of the first radiation detector.

According to a third aspect of the invention, in the radiography apparatus according to the first or second aspect, the second control unit may start the control for reading the charge accumulated in the pixels of the second radiation detector before the first control unit performs the control for reading the charge accumulated in the pixels of the first radiation detector.

According to a fourth aspect of the invention, in the radiography apparatus according to the third aspect, the first control unit may start the control for reading the charge accumulated in the pixels of the first radiation detector after the second control unit ends the control for reading the charge accumulated in the plurality of pixels of the second radiation detector.

According to a fifth aspect of the invention, in the radiography apparatus according to any one of the first to fourth aspects, an operation of the first control unit may be stopped while the second control unit is performing the control for reading the charge accumulated in the pixels of the second radiation detector.

According to a sixth aspect of the invention, in the radiography apparatus according to the fifth aspect, the operation of the first control unit may be stopped in a state in which the first control unit is turned on.

According to a seventh aspect of the invention, in the radiography apparatus according to any one of the first to sixth aspects, the second control unit may perform the control for reading the charge accumulated in the pixels of the second radiation detector for a longer period than the first control unit performs the control for reading the charge accumulated in the pixels of the first radiation detector.

According to an eighth aspect of the invention, in the radiography apparatus according to any one of the first to seventh aspects, the first control unit may perform control for transmitting image data obtained by reading the charge accumulated in the pixels of the first radiation detector to an external apparatus after the reading of the charge accumulated in each pixel of the first radiation detector and the second radiation detector ends and the second control unit may perform control for transmitting image data obtained by reading the charge accumulated in the pixels of the second radiation detector to the external apparatus after the reading of the charge accumulated in each pixel of the first radiation detector and the second radiation detector ends.

According to a ninth aspect of the invention, the radiography apparatus according to any one of the first to eighth aspects may further comprise a radiation limitation member that limits the transmission of the radiation between the first radiation detector and the second radiation detector.

According to a tenth aspect of the invention, in the radiography apparatus according to any one of the first to ninth aspects, each of the first radiation detector and the second radiation detector may comprise a light emitting layer that is irradiated with the radiation and emits light. The plurality of pixels of each of the first radiation detector and the second radiation detector may receive the light, generate the charge, and accumulate the charge. The light emitting layer of the first radiation detector and the light emitting layer of the second radiation detector may have different compositions.

According to an eleventh aspect of the invention, in the radiography apparatus according to any one of the first to ninth aspects, each of the first radiation detector and the second radiation detector may comprise a light emitting layer that is irradiated with the radiation and emits light and a substrate provided with the plurality of pixels which receive the light, generate the charge, and accumulate the charge. The substrate may be stacked on a side of the light emitting layer on which the radiation is incident.

According to a twelfth aspect of the invention, in the radiography apparatus according to the tenth or eleventh aspect, the light emitting layer of the first radiation detector may include CsI and the light emitting layer of the second radiation detector may include GOS.

According to a thirteenth aspect of the invention, there is provided a radiography method comprising: allowing a first control unit to perform control for reading charge accumulated in pixels of a first radiation detector that includes a plurality of pixels accumulating charge corresponding to emitted radiation in a state in which the charge is accumulated in the pixels of each of the first radiation detector and a second radiation detector that is provided so as to be stacked on a side of the first radiation detector opposite to a side on which the radiation is incident and includes a plurality of pixels accumulating charge corresponding to the emitted radiation; and allowing a second control unit to start control for reading the charge accumulated in the pixels of the second radiation detector in a state in which the charge is accumulated in the pixels of each of the first radiation detector and the second radiation detector at a time different from a time when the first control unit starts the control.

According to an embodiment of the invention, it is possible to provide a radiography apparatus and a radiography method that can reduce the influence of noise in a case in which charge accumulated in pixels of each of two radiation detectors is read.

DETAILED DESCRIPTION

Hereinafter, an embodiment of the present disclosure will be described in detail with reference to the drawings.

Figure 1:
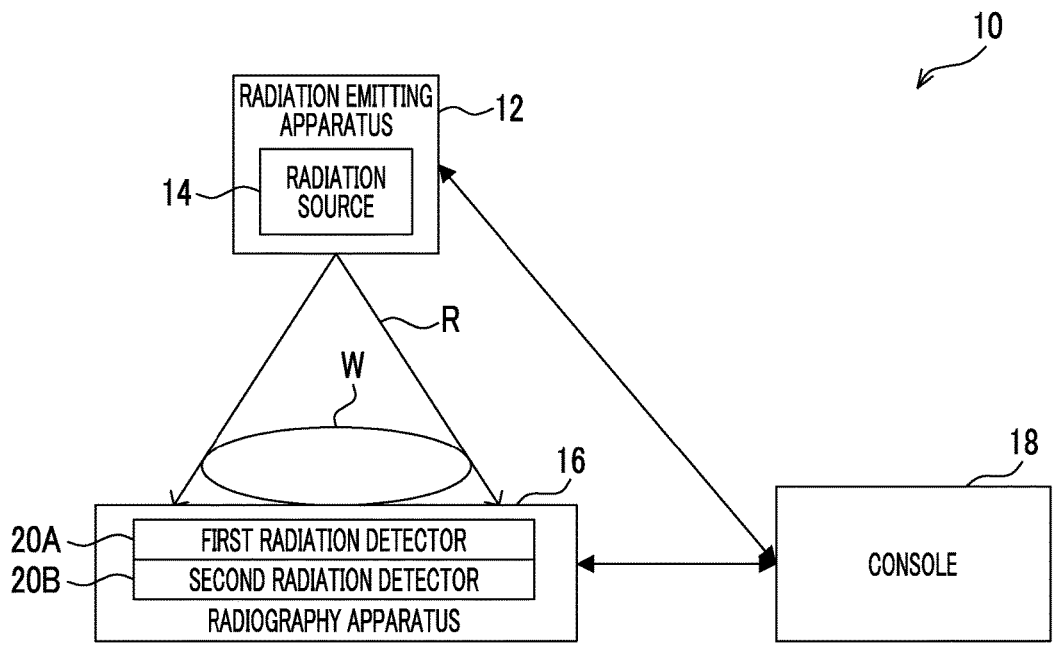
FIG. 1 is a block diagram illustrating an example of the configuration of a radiography system according to an embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

In a case in which the command to emit the radiation R is received, the radiation emitting apparatus 12 emits the radiation R from the radiation source 14 according to set emission conditions, such as a tube voltage, a tube current, and an irradiation period.

The radiography apparatus 16 according to this embodiment includes a first radiation detector 20A and a second radiation detector 20B that detect the radiation R which has been emitted from the radiation emitting apparatus 12 and then transmitted through the subject W. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

Figure 2:
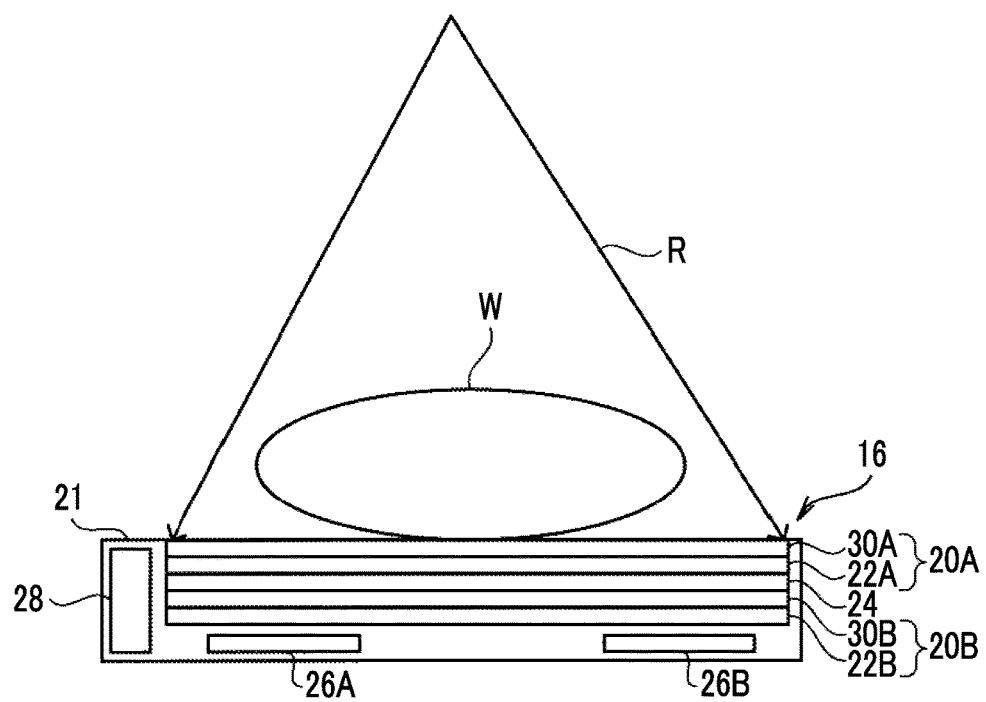
FIG. 2 is a cross-sectional view illustrating an example of the configuration of a radiography apparatus according to the embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes the first radiation detector 20A, the second radiation detector 20B, a radiation limitation member 24, a control substrate 26A, a control substrate 26B, and a case 28.

The first radiation detector 20A is provided on the incident side of the radiation R and the second radiation detector 20B is provided so as to be stacked on a side of the first radiation detector 20A opposite to the side on which the radiation R is incident. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) and the scintillator 22B includes gadolinium oxysulfide (GOS). In addition, a combination of the composition of the scintillator 22A and the composition of the scintillator 22B is not limited to the above-mentioned example and may be a combination of other compositions or a combination of the same compositions.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that the thickness of the radiation limitation member 24 is uniform in the range in which a variation in the thickness is equal to or less than 1%.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
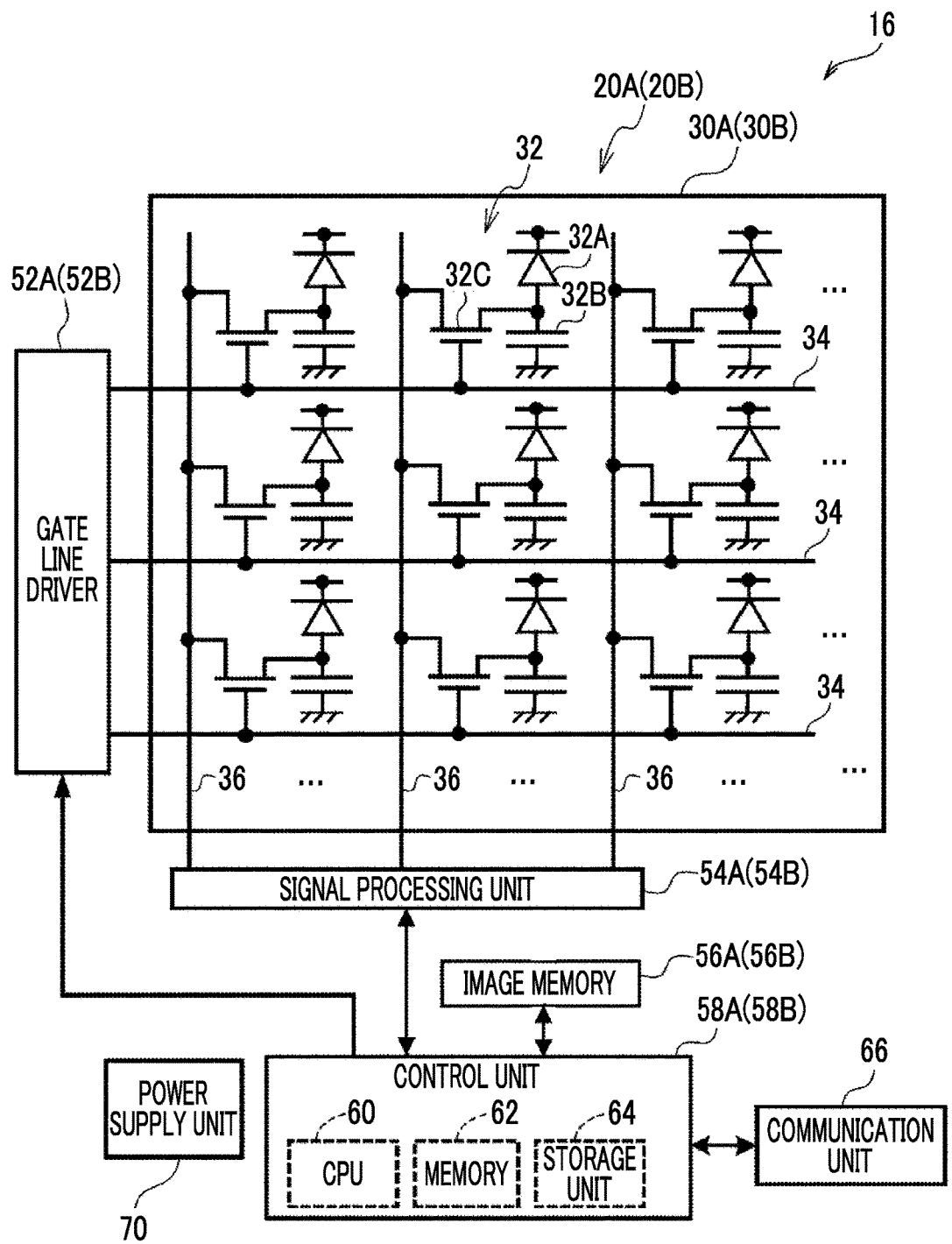
FIG. 3 is a block diagram illustrating an example of the configuration of a main portion of an electric system of the radiography apparatus according to the embodiment.

As illustrated in FIG. 3, a plurality of pixels 32 are two-dimensionally provided in one direction (a row direction in FIG. 3) and a cross direction (a column direction in FIG. 3) that crosses the one direction on the TFT substrate 30A. The pixel 32 includes a sensor unit 32A, a capacitor 32B, and a field effect thin film transistor (TFT; hereinafter, simply referred to as a "thin film transistor") 32C.

The sensor unit 32A includes, for example, an upper electrode, a lower electrode, and a photoelectric conversion film which are not illustrated, absorbs the light emitted from the scintillator 22A, and generates charge. The capacitor 32B accumulates the charge generated by the sensor unit 32A. The thin film transistor 32C converts the charge accumulated in the capacitor 32B into an electric signal and outputs the electric signal.

A plurality of gate lines 34 which extend in the one direction and are used to turn each thin film transistor 32C on and off are provided on the TFT substrate 30A. In addition, a plurality of data lines 36 which extend in the cross direction and which are used to read the charge through the thin film transistors 32C in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The rows of the thin film transistors 32C of the TFT substrate 30A are sequentially turned on by the electric signals which are supplied from the gate line driver 52A through the gate lines 34. Then, the charge which has been read by the thin film transistor 32C in an on state is transmitted as an electric signal through the data line 36 and is input to the signal processing unit 54A. In this way, charge is sequentially read from each row of the thin film transistors and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer (not illustrated) and an analog/digital (A/D) converter (not illustrated) are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A, and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B.

Figure 4:
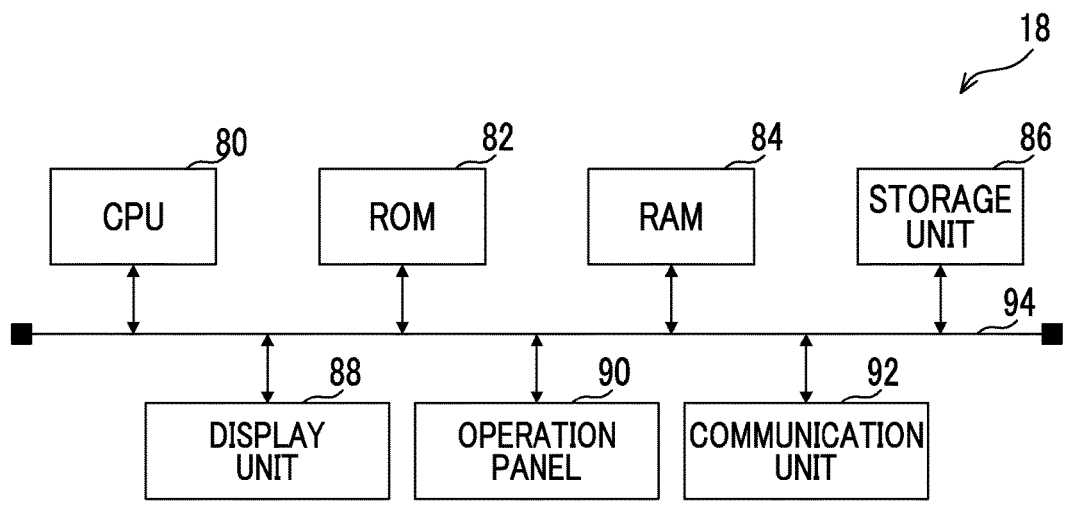
FIG. 4 is a block diagram illustrating an example of the configuration of a main portion of an electric system of a console according to the embodiment.

Next, the configuration of the console 18 according to this embodiment will be described with reference to FIG. 4. As illustrated in FIG. 4, the console 18 includes a CPU 80 that controls the overall operation of the console 18 and a ROM 82 in which, for example, various programs or various parameters are stored in advance. In addition, the console 18 includes a RAM 84 that is used as, for example, a work area in a case in which the CPU 80 executes various programs and a non-volatile storage unit 86 such as a hard disk drive (HDD).

The console 18 further includes a display unit 88 that displays, for example, an operation menu and a radiographic image obtained by imaging and an operation panel 90 which includes a plurality of keys and to which various kinds of information or operation commands are input. In addition, the console 18 includes a communication unit 92 that transmits and receives various kinds of information to and from the external apparatuses, such as the radiation emitting apparatus 12 and the radiography apparatus 16, using at least one of wireless communication or wired communication. The CPU 80, the ROM 82, the RAM 84, the storage unit 86, the display unit 88, the operation panel 90, and the communication unit 92 are connected to each other through a bus 94.

However, in the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has been transmitted through the first radiation detector 20A and reached the radiation limitation member 24 is absorbed by the radiation limitation member 24. About 50% of the radiation R that has been transmitted through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation (≈the amount of electric signal generated by the second radiation detector 20B) used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
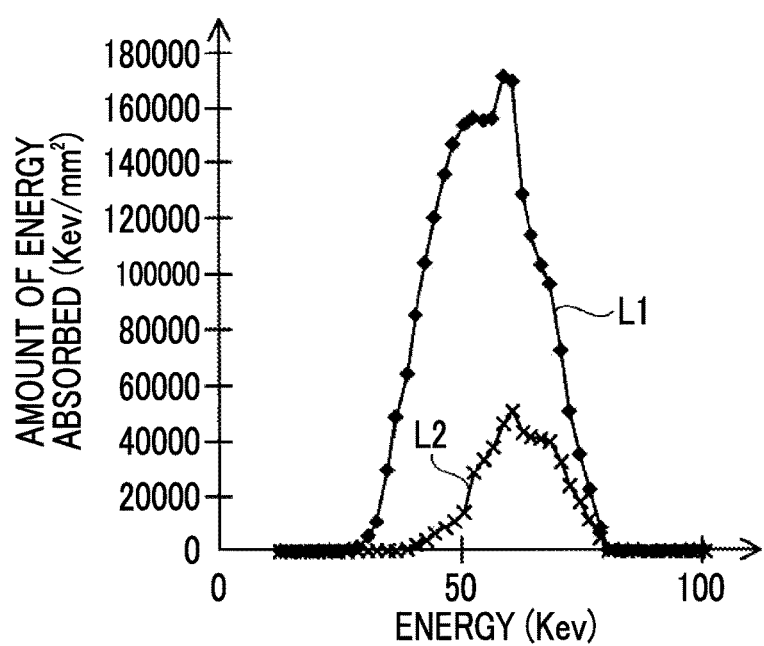
FIG. 5 is a graph illustrating the amount of radiation that reaches each of a first radiation detector and a second radiation detector according to the embodiment.

Low-energy components of the radiation R are absorbed first. Therefore, for example, as illustrated in FIG. 5, the energy components of the radiation R that reaches the second radiation detector 20B do not include the low-energy components of the energy components of the radiation R that reaches the first radiation detector 20A. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In FIG. 5, a solid line L2 indicates the relationship between the energy of the radiation R absorbed by the second radiation detector 20B and the amount of radiation R absorbed per unit area.

Figure 6:
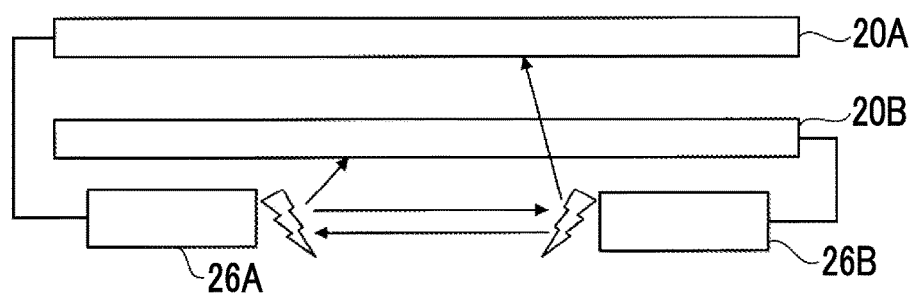
FIG. 6 is a diagram schematically illustrating electrical noise according to the embodiment.

For example, as illustrated in FIG. 6, an operation of reading the charge accumulated in the pixels 32 of one of the radiation detectors 20 causes noise in the other radiation detector 20. For example, the influence of noise is included in the electric signal generated by the second radiation detector 20B due to the electric signal generated by the operation of reading the charge accumulated in the pixels 32 of the first radiation detector 20A under the control of the control unit 58A of the control substrate 26A. In particular, since the amount of electric signal generated by the second radiation detector 20B is less than the amount of electric signal generated by the first radiation detector 20A, the electric signal is likely to be affected by the noise. In addition, an operation of transmitting image data indicating the radiographic image captured by one of the radiation detectors 20 to, for example, the console 18 causes noise in the other radiation detector 20.

Therefore, the radiography apparatus 16 according to this embodiment performs the following process in a state in which charge is accumulated in the pixels 32 of each radiation detector 20. That is, the radiography apparatus 16 starts to read the charge accumulated in the pixels 32 of the second radiation detector 20B at a time different from the time when the charge accumulated in the pixels 32 of the first radiation detector 20A starts to be read. Then, in a state in which the charge is held by the pixels 32 of one of the radiation detectors 20, the radiography apparatus 16 reads the charge accumulated in the pixels 32 of the other radiation detectors 20.

In this embodiment, the radiography apparatus 16 starts the reading of the charge accumulated in the pixels 32 of the second radiation detector 20B before the reading of the charge accumulated in the pixels 32 of the first radiation detector 20A. Then, after ending the reading of the charge accumulated in all of the pixels 32 of the second radiation detector 20B, the radiography apparatus 16 reads the charge accumulated in the pixels 32 of the first radiation detector 20A.

Figure 7:
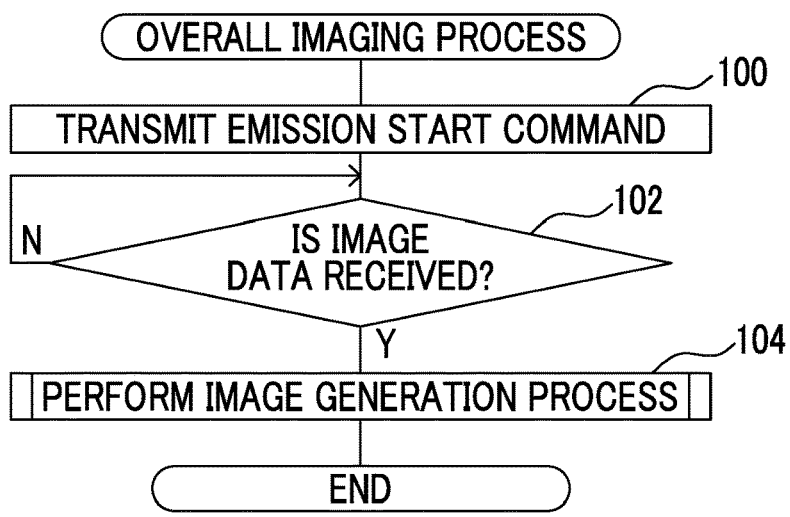
FIG. 7 is a flowchart illustrating the process flow of an overall imaging processing program according to the embodiment.

Next, the operation of the radiography system 10 according to this embodiment will be described with reference to FIGS. 7 to 10. FIG. 7 is a flowchart illustrating the process flow of an overall imaging processing program executed by the CPU 80 of the console 18 in a case in which the user inputs an imaging menu including, for example, the name of the subject W, an imaging part, and the emission conditions of the radiation R through the operation panel 90. The overall imaging processing program is installed in the ROM 82 of the console 18 in advance.

Figure 8:
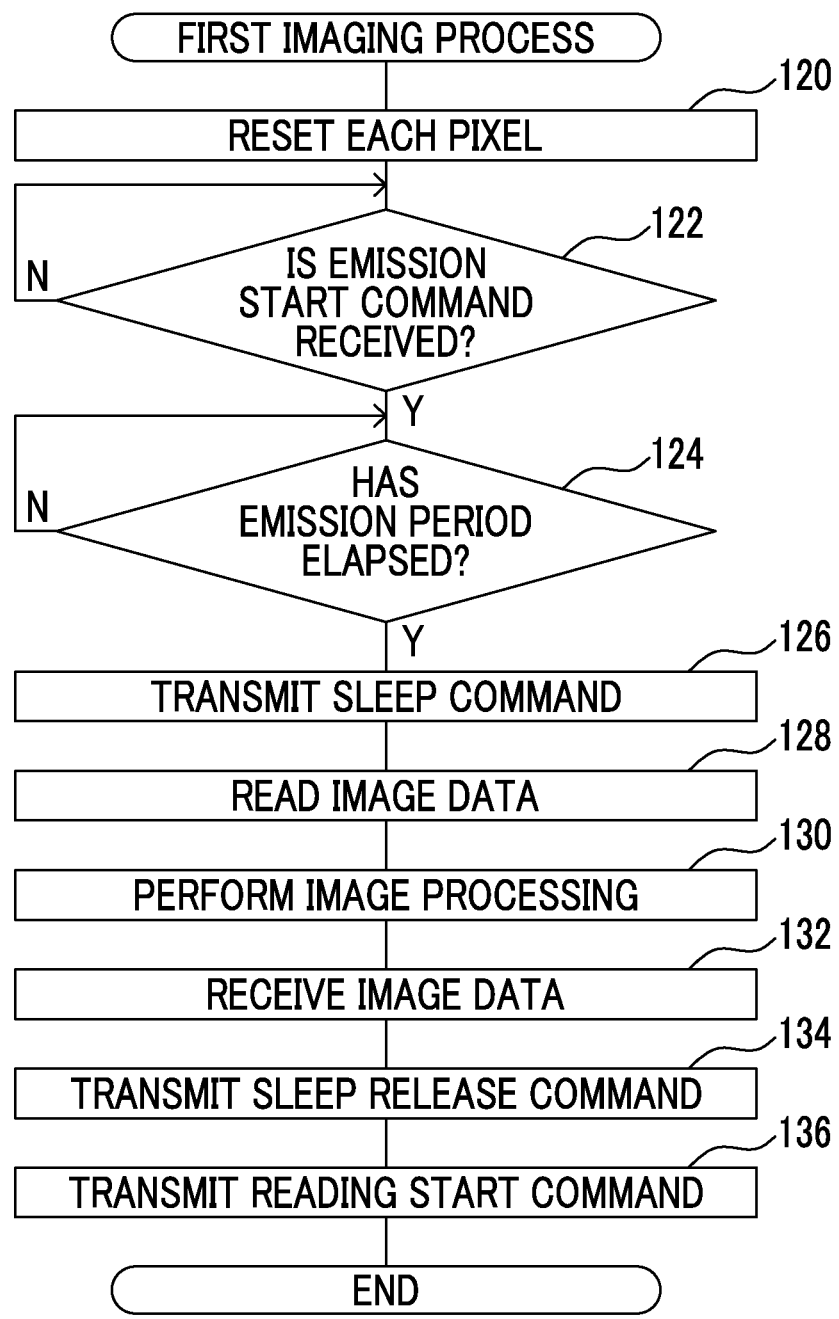
FIG. 8 is a flowchart illustrating the process flow of a first imaging processing program according to the embodiment.

FIG. 8 is a flowchart illustrating the process flow of a first imaging processing program executed by the control unit 58B of the radiography apparatus 16 in a case in which the radiography apparatus 16 is turned on. The first imaging processing program is installed in a ROM of the memory 62 of the control unit 58B in advance.

Figure 9:
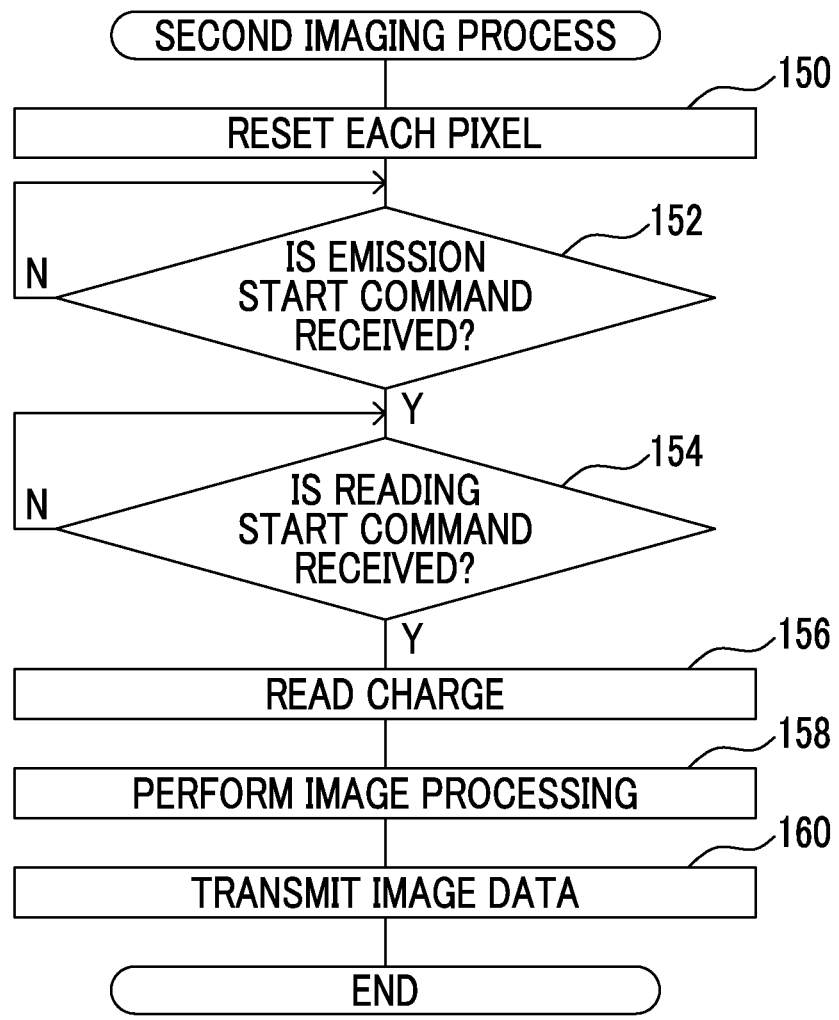
FIG. 9 is a flowchart illustrating the process flow of a second imaging processing program according to the embodiment.

FIG. 9 is a flowchart illustrating the process flow of a second imaging processing program executed by the control unit 58A of the radiography apparatus 16 in a case in which the radiography apparatus 16 is turned on. The second imaging processing program is installed in a ROM of the memory 62 of the control unit 58A in advance.

In Step 100 of FIG. 7, the CPU 80 transmits information included in the input imaging menu to the radiography apparatus 16 through the communication unit 92 and transmits the emission conditions of the radiation R to the radiation emitting apparatus 12 through the communication unit 92. Then, the CPU 80 transmits a command to start the emission of the radiation R to the radiography apparatus 16 and the radiation emitting apparatus 12 through the communication unit 92. In a case in which the emission conditions and the emission start command transmitted from the console 18 are received, the radiation emitting apparatus 12 starts the emission of the radiation R according to the received emission conditions. The radiation emitting apparatus 12 may include an irradiation button. In this case, the radiation emitting apparatus 12 receives the emission conditions and the emission start command transmitted from the console 18 and starts the emission of the radiation R according to the received emission conditions in a case in which the irradiation button is pressed.

Then, in Step 102, the CPU 80 waits until image data indicating the radiographic image captured by the first radiation detector 20A and image data indicating the radiographic image captured by the second radiation detector 20B are received. Hereinafter, the radiographic image captured by the first radiation detector 20A is referred to as a "first radiographic image" and the image data indicating the first radiographic image is referred to as "first radiographic image data". Hereinafter, the radiographic image captured by the second radiation detector 20B is referred to as a "second radiographic image" and the image data indicating the second radiographic image is referred to as "second radiographic image data". In a case in which the CPU 80 receives the first radiographic image data and the second radiographic image data through the communication unit 92, the determination result in Step 102 is "Yes" and the process proceeds to Step 104.

Figure 10:
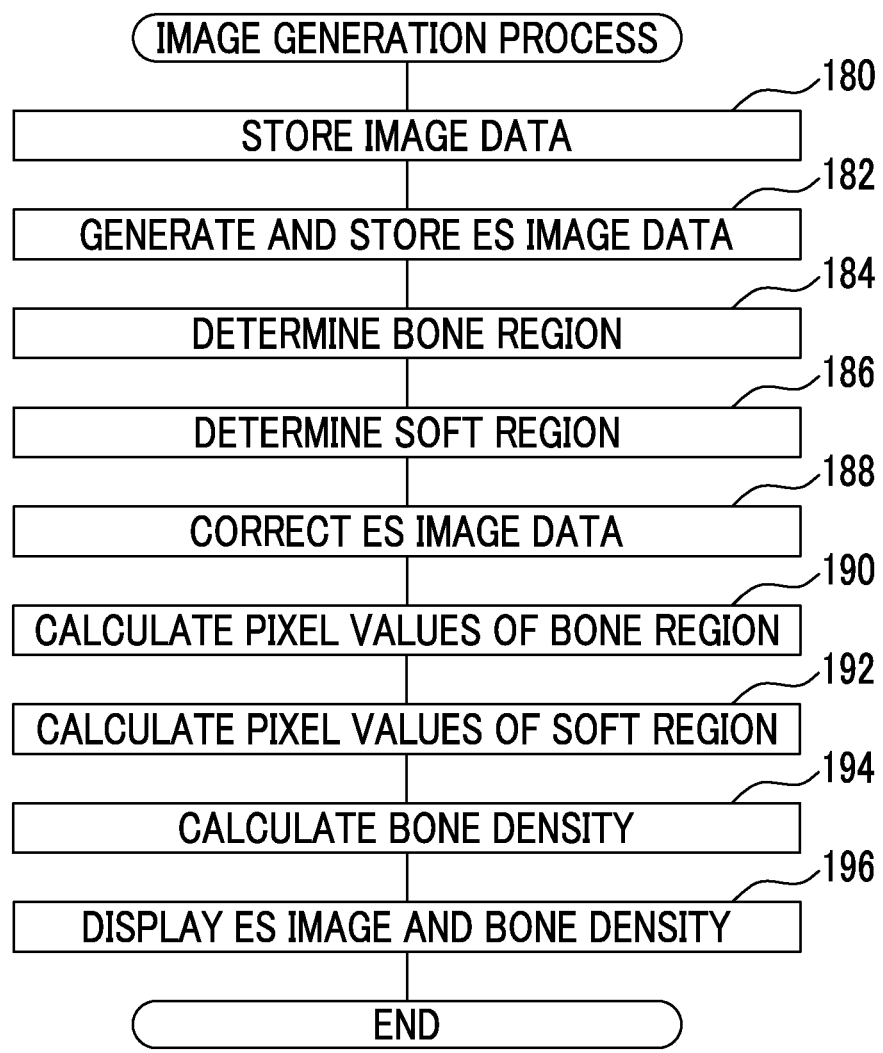
FIG. 10 is a flowchart illustrating the process flow of an image generation processing program according to the embodiment.

In Step 104, the CPU 80 performs an image generation process illustrated in FIG. 10 and ends the overall imaging process.

In Step 120 of FIG. 8, the control unit 58B performs a reset operation that reads the charge accumulated in the capacitor 32B of each pixel 32 of the second radiation detector 20B and removes the charge. In addition, the control unit 58B may perform the reset operation in Step 120 only once, may repeatedly perform the reset operation a predetermined number of times, or may repeatedly perform the reset operation until the determination result in Step 122 which will be described below becomes "Yes".

Then, in Step 122, the control unit 58B waits until a command to start the emission of the radiation R is received. In a case in which the control unit 58B receives the emission start command transmitted from the console 18 in Step 100 of the overall imaging process through the communication unit 66, the determination result in Step 122 is "Yes" and the process proceeds to Step 124. In a case in which the radiation emitting apparatus 12 includes an irradiation button and the control unit 58B receives the emission start command transmitted from the console 18 and information indicating that the irradiation button has been pressed through the communication unit 66, the determination result in Step 122 is "Yes". For example, in a case in which the irradiation button is pressed, the radiation emitting apparatus 12 may directly transmit information indicating that the irradiation button has been pressed to the radiography apparatus 16 or may transmit the information to the radiography apparatus 16 through the console 18. In Step 124, the control unit 58B waits for an emission period that is included in the information transmitted from the console 18 in Step 100 of the overall imaging process.

In Step 126, the control unit 58B transmits a command (hereinafter, referred to as a "sleep command") to change the control unit 58A to a state (so-called sleep state) in which the operation of the control unit 58A in an on state is stopped to the control unit 58A. In a case in which the sleep command transmitted in Step 126 is received, the control unit 58A interrupts the process performed until the sleep command is received and changes to the sleep state. Here, the sleep state is a state in which the CPU 60 of the control unit 58A performs only a process of receiving data through the communication unit 66 and is, for example, a state in which an operation based on an A/D conversion command and a communication control command is stopped and the previous state is maintained. In a case in which a further reduction in power consumption is desired, the supply of power to components other than the components required for the receiving process in the control substrate 26A may be stopped. In addition, while the control unit 58A is in the sleep state, charge can be accumulated in each pixel 32 of the first radiation detector 20A.

Then, in Step 128, the control unit 58B controls the gate line driver 52B such that the gate line driver 52B sequentially outputs an on signal to each gate line 34 of the second radiation detector 20B for a predetermined period. Then, the rows of the thin film transistors 32C connected to each gate line 34 are sequentially turned on and the charge accumulated in each capacitor 32B in each row sequentially flows as an electric signal to each data line 36. Then, the electric signal which has flowed to each data line 36 is converted into digital image data by the signal processing unit 54B and is stored in the image memory 56B.

In this embodiment, the control unit 58B repeatedly performs the above-mentioned on signal output process a plurality of times. The image data which has been repeatedly read from the second radiation detector 20B stores image data indicating one image in image memory 56B.

As such, in this embodiment, the reading of the charge accumulated in the pixels 32 of the second radiation detector 20B is performed a plurality of times. In a case in which the reading of the charge is performed a plurality of times, the influence of noise caused by the reading operation on image quality is more than that in a case in which the reading of charge is performed only once, but the charge accumulated in the pixels 32 of the second radiation detector 20B is prevented from remaining without being read. In this embodiment, the number of times the charge accumulated in the pixels 32 of the second radiation detector 20B is repeatedly read is predetermined in the range in which (the influence of the charge that remains without being read on image quality)>(the influence of noise caused by the reading operation on image quality) is satisfied.

Then, in Step 130, the control unit 58B performs image processing for performing various correction processes, such as offset correction and gain correction, for the image data stored in the image memory 56B in Step 128. Then, in Step 132, the control unit 58B transmits the image data (second radiographic image data) subjected to the image processing in Step 130 to the console 18 through the communication unit 66.

Then, in Step 134, the control unit 58B transmits a command (hereinafter, referred to as a "sleep release command") to release the sleep state of the control unit 58A to the control unit 58A. In a case in which the sleep release command transmitted in Step 134 is received, the control unit 58A returns from the sleep state and resumes the interrupted process. Then, in Step 136, the control unit 58B transmits a command (hereinafter, referred to as a "reading start command") to start the reading of image data to the control unit 58A and ends the first imaging process.

In Step 150 of FIG. 9, the control unit 58A performs a reset operation of reading the charge accumulated in the capacitor 32B of each pixel 32 of the first radiation detector 20A and removes the charge. In addition, the control unit 58A may perform the reset operation in Step 150 only once, may repeatedly perform the reset operation a plurality of times that are determined in advance, or may repeatedly perform the reset operation until the determination result in Step 152, which will be described below, becomes "Yes".

Then, in Step 152, the control unit 58A waits until a command to start the emission of the radiation R is received. In a case in which the control unit 58A receives the emission start command transmitted from the console 18 in Step 100 of the overall imaging process through the communication unit 66, the determination result in Step 152 is "Yes" and the process proceeds to Step 154. In a case in which the radiation emitting apparatus 12 includes an irradiation button and the control unit 58A receives the emission start command transmitted from the console 18 and information indicating that the irradiation button has been pressed through the communication unit 66, the determination result in Step 152 is "Yes". For example, in a case in which the irradiation button is pressed, the radiation emitting apparatus 12 may directly transmit information indicating that the irradiation button has been pressed to the radiography apparatus 16 or may transmit the information to the radiography apparatus 16 through the console 18. In Step 154, the control unit 58A waits until a reading start command is received. In a case in which the control unit 58A receives the reading start command transmitted from the control unit 58B in Step 136 of the first imaging process, the determination result in Step 154 is "Yes" and the process proceeds to Step 156.

Then, in Step 156, the control unit 58A controls the gate line driver 52A such that the gate line driver 52A sequentially outputs an on signal to each gate line 34 of the first radiation detector 20A for the above-mentioned predetermined period. Then, the rows of the thin film transistors 32C connected to each gate line 34 are sequentially turned on and the charge accumulated in each capacitor 32B in each row sequentially flows as an electric signal to each data line 36. Then, the electric signal which has flowed to each data line 36 is converted into digital image data by the signal processing unit 54A and is stored in the image memory 56A.

Then, in Step 158, the control unit 58A performs image processing for performing various correction processes, such as offset correction and gain correction, for the image data stored in the image memory 56A in Step 156. Then, in Step 160, the control unit 58A transmits the image data (first radiographic image data) subjected to the image processing in Step 158 to the console 18 through the communication unit 66.

In a case in which the console 18 receives the second radiographic image data transmitted in Step 132 and the first radiographic image data transmitted in Step 160, the determination result in Step 102 is "Yes" and an image generation process illustrated in FIG. 10 is performed.

In Step 180 of FIG. 10, the CPU 80 stores the first radiographic image data and the second radiographic image data received in Step 102 in each storage unit 86. Then, in Step 182, the CPU 80 generates image data indicating an energy subtraction image, using the first radiographic image data and the second radiographic image data received in Step 102 and stores the image data in the storage unit 86. Hereinafter, the energy subtraction image is referred to as an "ES image" and the image data indicating the energy subtraction image is referred to as "ES image data".

In this embodiment, the CPU 80 subtracts image data obtained by multiplying the first radiographic image data by a predetermined coefficient from image data obtained by multiplying the second radiographic image data by a predetermined coefficient for each corresponding pixel. The CPU 80 generates ES image data indicating an ES image in which soft tissues have been removed and bone tissues have been highlighted, using the subtraction. A method for determining the corresponding pixels of the first radiographic image data and the second radiographic image data is not particularly limited. For example, the amount of positional deviation between the first radiographic image data and the second radiographic image data, which are captured by the radiography apparatus 16 in a state in which a marker is put in advance, may be calculated from the difference between the positions of the marker in the first radiographic image data and the second radiographic image data. Then, the corresponding pixels of the first radiographic image data and the second radiographic image data may be determined on the basis of the calculated amount of positional deviation.

In this case, for example, the amount of positional deviation between the first radiographic image data and the second radiographic image data, which are obtained by capturing the image of both the subject W and the marker in a case in which the image of the subject W is captured, may be calculated from the difference between the positions of the marker in the first radiographic image data and the second radiographic image data. In addition, for example, the amount of positional deviation between the first radiographic image data and the second radiographic image data may be calculated on the basis of the structure of the subject W in the first radiographic image data and the second radiographic image data obtained by capturing the image of the subject W.

Then, in Step S184, the CPU 80 determines a bone tissue region (hereinafter, referred to as a "bone region") in the ES image that is indicated by the ES image data generated in Step S182. In this embodiment, for example, the CPU 80 estimates the approximate range of the bone region on the basis of the imaging part included in the imaging menu. Then, the CPU 80 detects pixels that are disposed in the vicinity of the pixels, of which the differential values are equal to or greater than a predetermined value, as the pixels forming the edge (end) of the bone region in the estimated range to determine the bone region.

Figure 11:
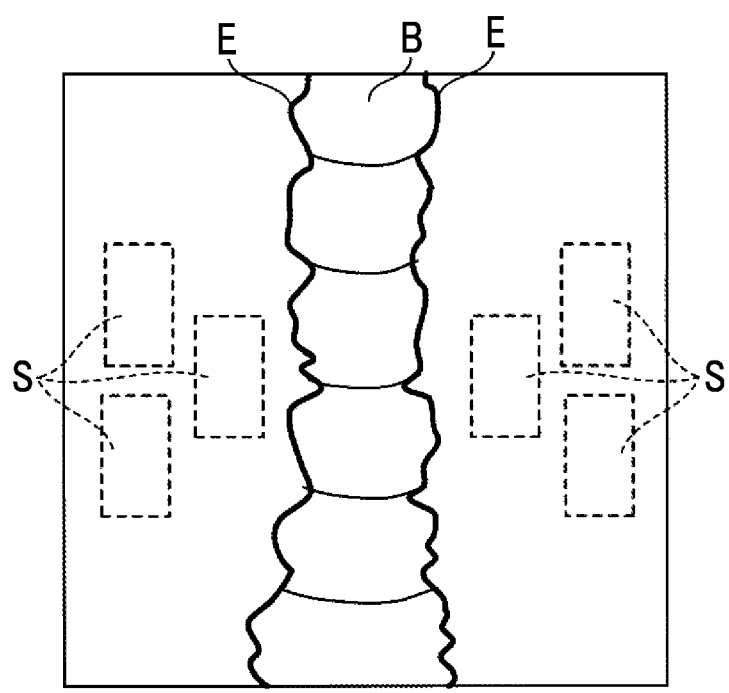
FIG. 11 is a front view schematically illustrating a bone tissue region and a soft tissue region according to the embodiment.

For example, as illustrated in FIG. 11, in Step S184, the CPU 80 detects the edge E of a bone region B and determines a region in the edge E as the bone region B. For example, FIG. 11 illustrates an ES image in a case in which the image of a backbone part of the upper half of the body of the subject W is captured.

A method for determining the bone region B is not limited to the above-mentioned example. For example, the CPU 80 displays the ES image that is indicated by the ES image data generated in Step S182 on the display unit 88. The user designates the edge E of the bone region B in the ES image displayed on the display unit 88 through the operation panel 90. Then, the CPU 80 may determine a region in the edge E designated by the user as the bone region B.

The CPU 80 may display an image in which the ES image and the edge E determined in Step S184 overlap each other on the display unit 88. In a case in which it is necessary to correct the edge E displayed on the display unit 88, the user corrects the position of the edge E through the operation panel 90. Then, the CPU 80 may determine a region in the edge E corrected by the user as the bone region B.

Then, in Step S186, the CPU 80 determines a soft tissue region (hereinafter, referred to as a "soft region") in the ES image that is indicated by the ES image data generated in Step S182. In this embodiment, for example, the CPU 80 determines a region, which is other than the bone region B and has a predetermined area including pixels at positions that are separated from the edge E by a distance corresponding to a predetermined number of pixels in a predetermined direction, as the soft region. For example, as illustrated in FIG. 11, in Step S186, the CPU 80 determines a plurality of (in the example illustrated in FIG. 11, six) soft regions S.

The predetermined direction and the predetermined number of pixels may be predetermined by, for example, experiments using the actual radiography apparatus 16 according to the imaging part. The predetermined area may be predetermined or may be designated by the user. In addition, for example, the CPU 80 may determine, as the soft region S, the pixels with pixel values in a predetermined range having the minimum pixel value (a pixel value corresponding to a position where the body thickness of the subject W is the maximum except the bone region B) as the lower limit in the ES image data. In addition, it goes without saying that the number of soft regions S determined in Step S186 is not limited to that illustrated in FIG. 11.

Then, in Step S188, the CPU 80 corrects the ES image data generated in Step S182 such that a variation in the ES image in each imaging operation is within an allowable range. In this embodiment, for example, the CPU 80 performs a correction process of removing image blur in the entire frequency band of the ES image data. The image data corrected in Step S188 is used to calculate bone density in a process from Step S190 to Step S194 which will be described below. Therefore, hereinafter, the corrected image data is referred to as "dual-energy X-ray absorptiometry (DXA) image data".

Then, in Step S190, the CPU 80 calculates an average value A1 of the pixel values of the bone region B in the DXA image data. Then, in Step S192, the CPU 80 calculates an average value A2 of the pixel values of all of the soft regions S in the DXA image data. Here, in this embodiment, for example, the CPU 80 performs weighting such that the soft region S which is further away from the edge E has a smaller pixel value and calculates the average value A2. Before the average values A1 and A2 are calculated in Step S190 and Step S192, respectively, abnormal values of the pixel values of the bone region B and the pixel values of the soft region S may be removed by, for example, a median filter.

Then, in Step S194, the CPU 80 calculates the bone density of the imaging part of the subject W. In this embodiment, for example, the CPU 80 calculates the difference between the average value A1 calculated in Step S190 and the average value A2 calculated in Step S192. In addition, the CPU 80 multiplies the calculated difference by a conversion coefficient for converting the pixel value into bone mass [g] to calculate the bone mass. Then, the CPU 80 divides the calculated bone mass by the area [cm$^2$] of the bone region B to calculate bone density [g/cm$^2$]. The conversion coefficient may be predetermined by, for example, experiments using the actual radiography apparatus 16 according to the imaging part.

Then, in Step S196, the CPU 80 displays the ES image indicated by the ES image data generated in Step S182 and the bone density calculated in Step S194 on the display unit 88 and then ends the image generation process.

Figure 12:
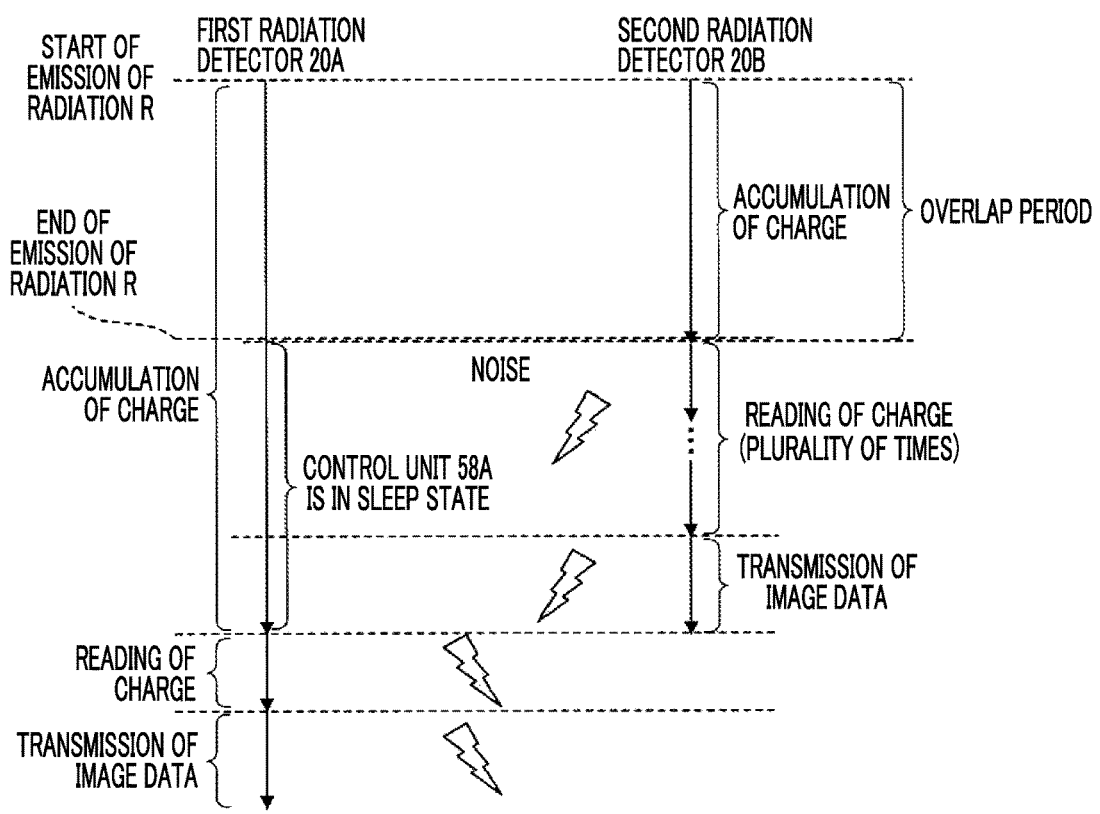
FIG. 12 is a timing chart illustrating an example of a radiography process according to the embodiment.

FIG. 12 illustrates an example of a timing chart illustrating the radiography process of the radiography apparatus 16 by the above-mentioned first and second imaging processes. As illustrated in FIG. 12, in a case in which the console 18 transmits an emission start command to the radiography apparatus 16 and the radiation emitting apparatus 12 in Step 100, the radiation emitting apparatus 12 starts the emission of the radiation R. In a case in which the emission start command transmitted from the console 18 is received, the control unit 58B of the radiography apparatus 16 stops the reset operation in the second radiation detector 20B and starts the accumulation of charge. In addition, in a case in which the emission start command transmitted from the console 18 is received, the control unit 58A of the radiography apparatus 16 stops the reset operation in the first radiation detector 20A and starts the accumulation of charge.

Then, in a case in which the emission period elapses, the radiation emitting apparatus 12 stops the emission of the radiation R. In a case in which the emission period elapses, the determination result in Step 124 is "Yes" and the control unit 58B transmits a sleep command to the control unit 58A in Step 126. In a case in which the command transmitted from the control unit 58B is received, the control unit 58A changes to the sleep state. After transmitting the sleep command to the control unit 58A, the control unit 58B reads the charge accumulated in the second radiation detector 20B a plurality of times and acquires image data in Step 128.

Then, the control unit 58B transmits the second radiographic image data captured by the second radiation detector 20B to the console 18 in Step 132 and transmits a sleep release command to the control unit 58A in Step 134. In a case in which the sleep release command transmitted from the control unit 58B is received, the control unit 58A returns from the sleep state. In addition, after transmitting the sleep release command to the control unit 58A, the control unit 58B transmits a reading start command to the control unit 58A in Step 136.

In a case in which the reading start command transmitted from the control unit 58B is received, the determination result in Step 154 is "Yes" and the control unit 58A reads the charge accumulated in the first radiation detector 20A and acquires image data in Step 156. Then, the control unit 58A transmits the first radiographic image data captured by the first radiation detector 20A to the console 18 in Step 160.

That is, as illustrated in FIG. 12, in the radiography apparatus 16 according to this embodiment, the periods for which the first radiation detector 20A and the second radiation detector 20B accumulate charge in the pixels 32 overlap each other.

Then, the radiography apparatus 16 reads the charge accumulated in the pixels 32 of the second radiation detector 20B first in a state in which charge is continuously accumulated in the pixels 32 of the first radiation detector 20A and transmits the second radiographic image data to the console 18. In addition, in a case in which the transmission of the second radiographic image data to the console 18 ends, the radiography apparatus 16 reads the charge accumulated in the pixels 32 of the first radiation detector 20A and transmits the first radiographic image data to the console 18. Therefore, the influence of noise on the second radiographic image indicated by the second radiographic image data which is caused by the reading of the charge accumulated in the pixels 32 of the first radiation detector 20A and the transmission of the first radiographic image data to the console 18 is prevented.

As described above, according to this embodiment, in a state in which charge is accumulated in each pixel 32 of the first radiation detector 20A and the second radiation detector 20B, the charge accumulated in each pixel 32 of the first radiation detector 20A and the second radiation detector 20B is read by the following process. That is, the reading of the charge accumulated in the pixels 32 of one of the first radiation detector 20A and the second radiation detector 20B starts first. While the charge accumulated in the pixels 32 of one of the first radiation detector 20A and the second radiation detector 20B is being read, the reading of the charge accumulated in the pixels 32 of the other radiation detector is not performed. Therefore, it is possible to reduce the influence of noise in a case in which the charge accumulated in each pixel of two radiation detectors is read.

In addition, according to this embodiment, the charge accumulated in the pixels 32 of the second radiation detector 20B starts to be read before the charge accumulated in the pixels 32 of the first radiation detector 20A is read. After the reading of the charge accumulated in all of the pixels 32 of the second radiation detector 20B ends, the reading of the charge accumulated in the pixels 32 of the first radiation detector 20A starts. As described above, the amount of electric signal generated in the second radiation detector 20B in a case in which a radiographic image is captured is less than the amount of electric signal generated in the first radiation detector 20A. That is, the electric signal generated in the second radiation detector 20B is more likely to be affected by noise than the electric signal generated in the first radiation detector 20A.

In contrast, in this embodiment, after the capture of a radiographic image by the second radiation detector 20B ends, the reading of the charge accumulated in the pixels 32 of the first radiation detector 20A starts. Therefore, it is possible to reduce the influence of noise in a case in which the charge accumulated in each pixel of two radiation detectors is read.

According to this embodiment, while the charge accumulated in the pixels 32 of the second radiation detector 20B is being read, the first control unit 58A is in the sleep state. Therefore, after the capture of a radiographic image by the second radiation detector 20B, the reading of the charge accumulated in the pixels 32 of the first radiation detector 20A can start earlier than that in a case in which the first control unit 58A is in an off state.

In addition, according to this embodiment, while the charge accumulated in the pixels 32 of the first radiation detector 20A is being read and while the charge accumulated in the pixels 32 of the second radiation detector 20B is being read, the process is performed as follows. That is, according to this embodiment, while the charge is being read, the transmission of the first radiographic image data to the console 18 and the transmission of the second radiographic image data to the console 18 are not performed.

In a case in which image data is transmitted from the radiography apparatus 16 to an external apparatus, such as the console 18 while charge is being read from the pixels 32, noise is likely to overlap the read electric signal. Particularly, in the case of wireless communication, noise is more likely to overlap than that in the case of wired communication. Therefore, according to this embodiment, it is possible to reduce the influence of noise associated with the transmission of image data.

In the above-described embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B.

In the above-described embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In the above-described embodiment, the case in which the charge accumulated in the pixels 32 of the second radiation detector 20B is read before the charge accumulated in the pixels 32 of the first radiation detector 20A is read has been described. However, the invention is not limited thereto. For example, the case in which the charge accumulated in the pixels 32 of the second radiation detector 20B is read before the charge accumulated in the pixels 32 of the first radiation detector 20A. For example, the charge accumulated in the pixels 32 of the first radiation detector 20A and the charge accumulated in the pixels 32 of the second radiation detector 20B may be alternately read for every predetermined number of rows. In any of these cases, while the charge accumulated in the pixels 32 of one of the first radiation detector 20A and the second radiation detector 20B is being read, the reading of the charge accumulated in the pixels 32 of the other radiation detector is not performed.

In the above-described embodiment, the case in which, after the second radiographic image data captured by the second radiation detector 20B is transmitted to the console 18, the reading of the charge accumulated in the pixels 32 of the first radiation detector 20A starts has been described. However, the invention is not limited thereto. For example, while the process in Step 130 is being performed, the reading of the charge accumulated in the pixels 32 of the first radiation detector 20A may start. In this case, an aspect in which the process in Step 134 and Step 136 is performed between Step 128 and Step 130 is given as an example. For example, after a predetermined period elapses since the reading of the charge accumulated in the pixels 32 of the second radiation detector 20B has started, the reading of the charge accumulated in the pixels 32 of the first radiation detector 20A may start.

In the above-described embodiment, the case in which the charge accumulated in the pixels 32 of the second radiation detector 20B is repeatedly read a plurality of times has been described. However, the invention is not limited thereto. For example, the sum of the periods for which the charge is repeatedly read a plurality of times may be one reading period and the charge accumulated in the pixels 32 of the second radiation detector 20B may be read once.

Figure 13:
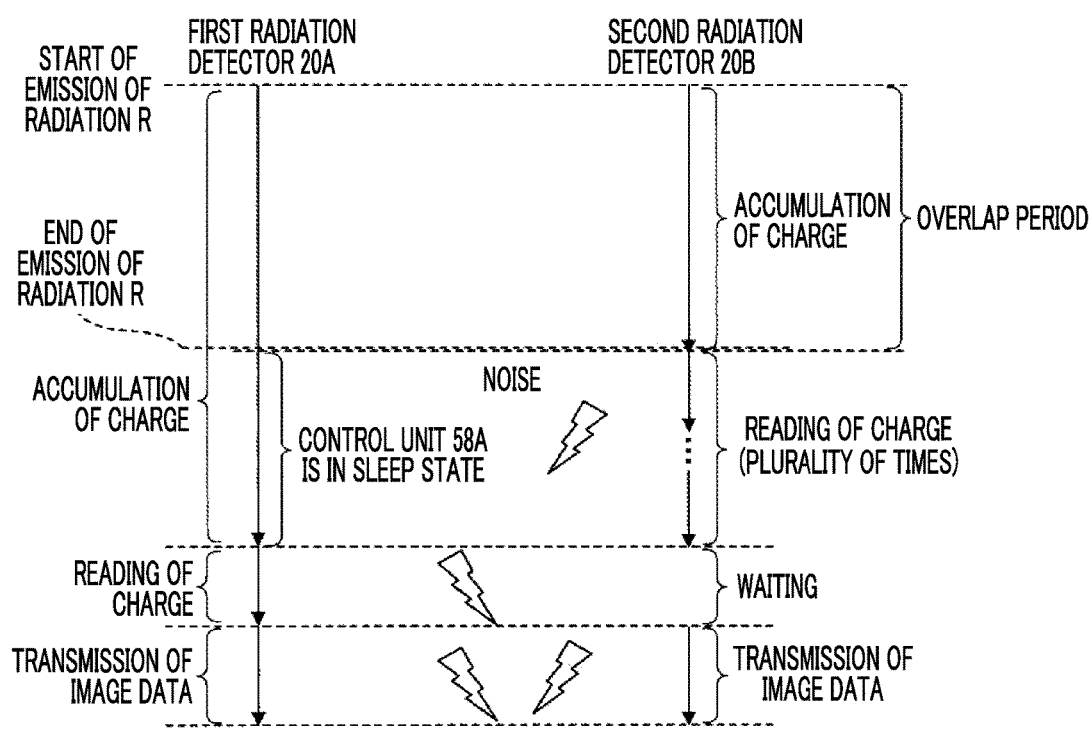
FIG. 13 is a timing chart illustrating an example of a radiography process according to a modification example.

In the above-described embodiment, the case in which the image data captured by the second radiation detector 20B and the image data captured by the first radiation detector 20A are transmitted to the console 18 at different times has been described. However, the invention is not limited thereto. For example, as illustrated in FIG. 13, after the charge accumulated in the pixels 32 of each radiation detector 20 is read, each of the read image data items may be transmitted to the console 18.

In the above-described embodiment, the case in which the control unit 58A and the control unit 58B transmit and receive various commands to control, for example, the change to the sleep state, the release of the sleep state, and the order in which the charge accumulated in the pixels 32 of the radiation detector 20 is read has been described. However, the invention is not limited thereto. For example, the control process may be performed under the control of the console 18.

In this case, for example, after the emission period elapses since the emission start command has been transmitted, the CPU 80 of the console 18 may transmit the sleep command to the control unit 58A of the radiography apparatus 16. Then, the CPU 80 transmits the reading start command to the control unit 58B of the radiography apparatus 16 at the same time as the sleep command is transmitted. In a case in which the reading start command transmitted from the console 18 is received, the control unit 58B performs the same process as that from Step 128 to Step 132 to transmit the second radiographic image data to the console 18.

In a case in which the first radiographic image data transmitted from the control unit 58B is received, the CPU 80 transmits the sleep release command to the control unit 58A and then transmits the reading start command to the control unit 58A. In a case in which the sleep release command transmitted from the console 18 is received, the control unit 58A returns from the sleep state. In addition, in a case in which the reading start command transmitted from the console 18 is received, the control unit 58A performs the same process as that from Step 156 to Step 160 to transmit the first radiographic image data to the console 18.

Then, in a case in which the first radiographic image data and the second radiographic image data are received, the CPU 80 performs the image generation process illustrated in FIG. 10 in Step 104.

For example, the control unit 58A may transmit the reading start command to the control unit 58B and may change to the sleep state. In a case in which the reading start command is received from the control unit 58A, the control unit 58B performs the process from Step 128 to Step 134. Then, in a case in which the sleep release command transmitted from the control unit 58B in Step 134 is received, the control unit 58A performs the process from Step 156 to Step 160.

In the above-described embodiment, the case in which the radiography apparatus 16 is controlled by two control units (control units 58A and 58B) has been described. However, the invention is not limited thereto. For example, the radiography apparatus 16 may be controlled by one control unit.

In the above-described embodiment, the aspect in which the overall imaging processing program is stored (installed) in the ROM 82 in advance has been described. However, the invention is not limited thereto. The overall imaging processing program may be recorded on a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through a network.

In the above-described embodiment, the aspect in which the first imaging processing program is stored in the ROM of the memory 62 of the control unit 58B in advance and the second imaging processing program is stored in the ROM of the memory 62 of the control unit 58A in advance has been described. However, the invention is not limited thereto. The first imaging processing program and the second imaging processing program may be recorded on the above-mentioned recording medium and then provided. In addition, the first imaging processing program and the second imaging processing program may be downloaded from an external apparatus through the network.

The disclosure of Japanese Patent Application No. 2016-063951, filed on Mar. 28, 2016, is incorporated herein by reference in its entirety.

All publications, patent applications, and technical standards mentioned in this specification are herein incorporated by reference to the same extent as if each individual publication, patent application, or technical standard is specifically and individually indicated to be incorporated by reference.

Explanation of References

What is claimed is:

1. A radiography apparatus comprising:
    a first radiation detector that includes a plurality of pixels accumulating charge corresponding to emitted radiation;
    a second radiation detector that is provided so as to be stacked on a side of the first radiation detector opposite to a side on which the radiation is incident and includes a plurality of pixels accumulating charge corresponding to the emitted radiation;
    a first control unit that is configured to perform control for reading the charge accumulated in the pixels of the first radiation detector in a state in which the charge is accumulated in the pixels of each of the first radiation detector and the second radiation detector; and
    a second control unit that is configured to start control for reading the charge accumulated in the pixels of the second radiation detector in a state in which the charge is accumulated in the pixels of each of the first radiation detector and the second radiation detector at a time different from a time when the first control unit starts the control;

wherein the first control unit is configured to perform control for reading the charge accumulated in the pixels of the first radiation detector in a state in which the charge is held in the pixels of the second radiation detector, and the second control unit is configured to perform control for reading the charge accumulated in the pixels of the second radiation detector in a state in which the charge is held in the pixels of the first radiation detector.

2. The radiography apparatus according to claim 1, wherein the second control unit is configured to start the control for reading the charge accumulated in the pixels of the second radiation detector before the first control unit performs the control for reading the charge accumulated in the pixels of the first radiation detector.

3. The radiography apparatus according to claim 2, wherein the first control unit is configured to start the control for reading the charge accumulated in the pixels of the first radiation detector after the second control unit ends the control for reading the charge accumulated in the plurality of pixels of the second radiation detector.

4. The radiography apparatus according to claim 1, wherein the first control unit is configured to stop operation while the second control unit is performing the control for reading the charge accumulated in the pixels of the second radiation detector.

5. The radiography apparatus according to claim 4, wherein the first control unit is configured to stop the operation in a state in which the first control unit is turned on.

6. The radiography apparatus according to claim 1, wherein the second control unit is configured to perform the control for reading the charge accumulated in the pixels of the second radiation detector for a longer period than the first control unit performs the control for reading the charge accumulated in the pixels of the first radiation detector.

7. The radiography apparatus according to claim 1, wherein the first control unit is configured to perform control for transmitting image data obtained by reading the charge accumulated in the pixels of the first radiation detector to an external apparatus after the reading of the charge accumulated in each pixel of the first radiation detector and the second radiation detector ends, and the second control unit is configured to perform control for transmitting image data obtained by reading the charge accumulated in the pixels of the second radiation detector to the external apparatus after the reading of the charge accumulated in each pixel of the first radiation detector and the second radiation detector ends.

8. The radiography apparatus according to claim 1, further comprising:

a radiation limitation member that limits the transmission of the radiation between the first radiation detector and the second radiation detector.

9. The radiography apparatus according to claim 1, wherein each of the first radiation detector and the second radiation detector comprises a light emitting layer that is irradiated with the radiation and emits light, the plurality of pixels of each of the first radiation detector and the second radiation detector receive the light, generate the charge, and accumulate the charge, and the light emitting layer of the first radiation detector and the light emitting layer of the second radiation detector have different compositions.

10. The radiography apparatus according to claim 1, wherein each of the first radiation detector and the second radiation detector comprises a light emitting layer that is irradiated with the radiation and emits light and a substrate provided with the plurality of pixels which receive the light, generate the charge, and accumulate the charge, and the substrate is stacked on a side of the light emitting layer on which the radiation is incident.

11. The radiography apparatus according to claim 9, wherein the light emitting layer of the first radiation detector includes CsI, and the light emitting layer of the second radiation detector includes GOS.

12. A radiography method comprising:

accumulating charge in pixels of each of a first radiation detector that includes a plurality of pixels accumulating charge corresponding to emitted radiation, and a second radiation detector that is provided so as to be stacked on a side of the first radiation detector opposite to a side on which the radiation is incident and includes a plurality of pixels accumulating charge corresponding to the emitted radiation;

allowing a first control unit to perform control for reading the charge accumulated in the pixels of the first radiation detector while accumulating the charge in the pixels of each of the first radiation detector and the second radiation detector; and allowing a second control unit to start control for reading the charge accumulated in the pixels of the second radiation detector while accumulating the charge in the pixels of each of the first radiation detector and the second radiation detector at a time different from a time when the first control unit starts the control;

wherein the first control unit is configured to perform control for reading the charge accumulated in the pixels of the first radiation detector in a state in which the charge is held in the pixels of the second radiation detector, and the second control unit is configured to perform control for reading the charge accumulated in the pixels of the second radiation detector in a state in which the charge is held in the pixels of the first radiation detector.

* * * * *